United States Patent [19]

Hitzig

[11] Patent Number: 5,792,163

[45] Date of Patent: Aug. 11, 1998

[54] LINEAR PUNCH

[76] Inventor: Gary Hitzig, 30 Cornwells Beach Rd., Port Washington, N.Y. 11050

[21] Appl. No.: 679,094

[22] Filed: Jul. 12, 1996

Related U.S. Application Data

[63] Continuation-in-part of Ser. No. 582,282, Jan. 3, 1996, abandoned.

[51] Int. Cl.⁶ ............................................. A61B 17/32
[52] U.S. Cl. ........................... 606/167; 600/562; 606/184
[58] Field of Search .................................. 606/187, 184, 606/185, 167, 170; 604/165, 164, 116; 128/754

[56] References Cited

U.S. PATENT DOCUMENTS

| 3,913,566 | 10/1975 | Lacey | 606/184 |
| 4,122,855 | 10/1978 | Tezel | 606/131 |
| 4,832,045 | 5/1989 | Goldberger | 606/184 |
| 5,183,053 | 2/1993 | Yeh et al. | 606/167 |
| 5,186,178 | 2/1993 | Yeh et al. | 606/167 |
| 5,439,475 | 8/1995 | Bennett | 606/187 |
| 5,507,565 | 4/1996 | Mott | 606/184 |
| 5,570,700 | 11/1996 | Vogeler | 606/184 |

FOREIGN PATENT DOCUMENTS

| 90022 | 7/1921 | Switzerland | 606/167 |

*Primary Examiner*—Robert A. Hafer
*Assistant Examiner*—Justine R. Yu
*Attorney, Agent, or Firm*—Ostrolenk, Faber, Gerb & Soffen, LLP

[57] ABSTRACT

A linear punch of unitary construction for use in transplanting hair follicles is provided. The linear punch includes an elongated oval shaped cutting edge at one end capable of cutting through scalp tissue. The cutting edge defines a hollow cavity having an outer wall structure that expands into a circular cross-section, thereby permitting an elongated oval incision to be made in the scalp of a hair transplant patient. The incision is capable of receiving hair follicles in a manner which allows the hair follicles to grow and flourish without compression or tufting. The incision also allows a surgeon to precisely fit the hair being grafted to the incisional site.

12 Claims, 1 Drawing Sheet

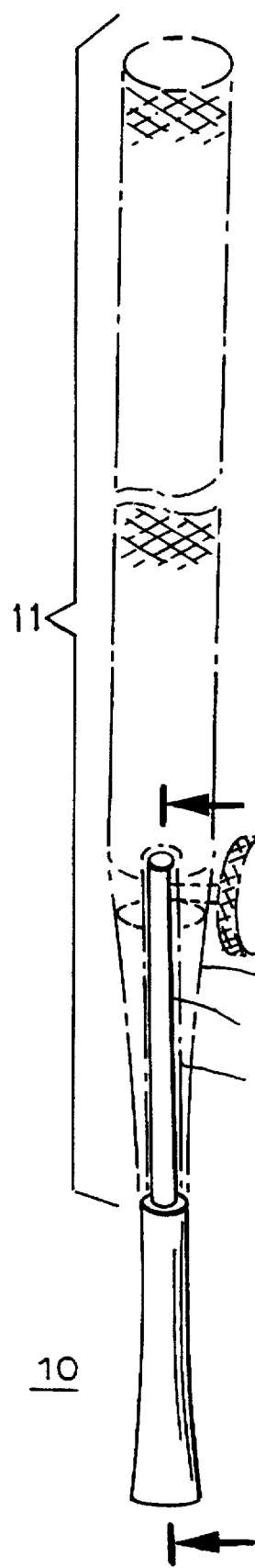
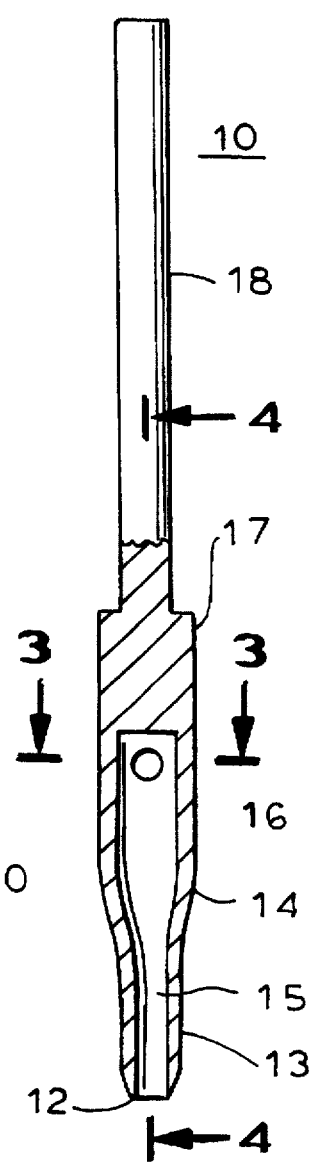
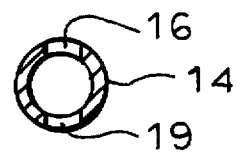
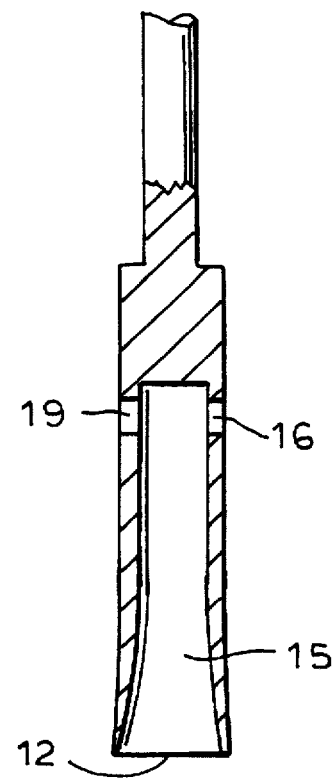
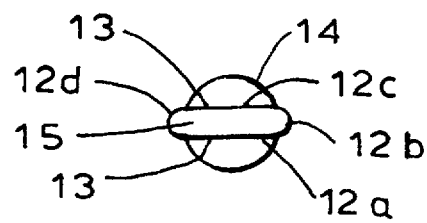

LINEAR PUNCH

This is a continuation-in-part of application Ser. No. 08/582,282 filed Jan. 3, 1996, now abandoned.

BACKGROUND AND OBJECTS OF THE INVENTION

This invention relates to a new and improved design as related to a linear punch for utilization in the science of transplanting of hair follicles in humans wherein hair follicles are taken from the donor area of a person's scalp and said hair follicles are transplanted into the recipient area of a person's scalp, said recipient area being an area where baldness is occurring. The design of the linear punch is such as to provide for a tool of unitary construction defining an elongated oval shaped cutting edge at one end thereof that lies in a single plane and that is capable of cutting through scalp tissue and which also defines a hollow cavity having an outer wall structure that expands into a circular cross section thereby providing the means to create an elongated oval incision in the scalp of an individual undergoing a hair transplantation. The elongated oval incision is capable of receiving transplanted strips of hair follicles in a manner and fashion that will cause the hair follicles to flourish and grow without compression or tufting of the transplanted hair follicles. This linear incision allows the surgeon to precisely fit the hair being grafted to the cite of the incision.

Although there exists the ability to transplant hair follicles from one area of the scalp of a human to another area thereof, the prior art techniques, methodology and the implements utilized in conjunction therewith do not address themselves to the instant invention and its unique design and advantages.

In conjunction with the prior art which addresses itself to tools capable of utilization in conjunction with hair transplantation, it should be noted that the following patents evidence the present state of the art as related thereto, same neither teaching nor disclosing the patentable features and/or patentable design of the present invention.

More particularly, the prior art referred to above is as follows: U.S. Pat. No. 3,512,519, entitled "Anatomical Biopsy Sample", issued to Hall on May 19, 1970; U.S. Pat. No. 3,561,449, entitled "Cutter Tool", issued to Bellantoni on Feb. 9, 1971; U.S. Pat. No. 3,683,892, entitled "Device for the Extraction of Core Samples", issued to Harris on Aug. 15, 1972; U.S. Pat. No. 3,913,566, entitled "Biopsy Tool and Method", issued to Lacey on Oct. 21, 1975; U.S. Pat. No. 4,122,855, entitled "Cutting Tool", issued to Jirayr Tezel on Oct. 31, 1978; U.S. Pat. No. 5,439,475, entitled "Tissue Grafting Method Using an Apparatus with Multiple Tissue Receiving Receptacles", issued to David M. Bennett on Aug. 8, 1995; and U.S. Pat. No. 5,183,053, entitled "Elliptical Biopsy Punch", issued to Charles R. Yeh and Donald H. Huldin on Feb. 2, 1993.

In keeping with the invention, it is a specific object thereto to create a new and improved linear punch that is simple in construction, unitary in design and whose use is facilitated by its design.

It is another object of the present invention to create a new and improved linear punch wherein the incision created by utilization of the linear punch allows for limited cutting of the scalp and thus nominally disturbs the scalp tissue.

It is another object of the present invention to create a new and improved linear punch wherein the incision made by the linear punch does not cause the blood vessels in the tissue underlying the surface of said scalp at the point of incision to be sealed as is the case with the use of a laser, but rather, allows for the implanted hair follicles to be readily bathed in tissue fluid thereby enhancing the viability and the survivability of the hair follicles that are the subject of the transplantation process.

It is another object of the present invention to create a new and improved linear punch which is capable of creating a unique incision in the form of an elongated oval that will not close thereby allowing for the insertion of hair follicles without causing the compression thereof once inserted.

It is another object of the present invention to create a new and improved linear punch which is capable of utilization to achieve the transplanting of hair follicles without the necessity of having expensive and/or extensive incision making equipment.

It is another object of the present invention to create a new and improved linear punch whose design facilitates the sterilization and thus the re-usability of the linear punch.

It is another object of the present invention to create a new and improved linear punch such as to allow for the easy removal from the area of the incision the scalp tissue that is cut by the linear punch.

It is another object of the present invention to create a new and improved linear punch that creates an incision that readily heals without diminishing the achieving of an overall appearance of one having as full a head of hair as possible in the area undergoing transplantation.

It is another object of the present invention to create a new and improved linear punch that creates an incision that allows for the precise fit of linear strip grafts created from the harvesting of hair follicles and avoids the compressing of inserted hair follicles once same are transplanted.

It is another object of the present invention to create a new and improved linear punch whose design allows for the easy insertion thereof into a hand held handle.

It is another object of the present invention to create a new and improved linear punch that is capable of creating a unique incision in the form of an elongated oval having parallel sides within the scalp capable of accepting a strip of human skin containing healthy hair follicles, The objects and advantages of the invention are set forth in part herein and in part will be obvious herefrom, or may be learned by practice of the invention, the same being realized and attained by means of the instrumentalities and combinations pointed out in the appended claims.

The invention consists in the novel parts, constructions, arrangements, combinations and improvements herein shown and described.

BRIEF DESCRIPTION OF THE DRAWINGS

FIG. 1 is a three-dimensional perspective view of the linear punch constructed in accordance with the invention wherein the linear punch is mounted onto a handle member, the handle member appearing in dashed lines and not forming a part of this invention.

FIG. 2 is a partial cross-sectional view of the linear punch as depicted in FIG. 1 as taken along line 2—2.

FIG. 3 is a cross-sectional view of the linear punch as depicted in FIG. 2 as taken along line 3—3.

FIG. 4 is a partial cross-sectional view of the linear punch as depicted in FIG. 2 and taken along line 4—4.

FIG. 5 is a bottom view of the linear punch constructed in accordance with the invention.

DESCRIPTION OF PREFERRED EMBODIMENT

Reference is now herein made to FIG. 1 wherein there is illustrated a three-dimensional perspective view of linear punch 10 as detachably affixed to handle 11.

It should be noted that handle 11 is an item of equipment well known in the prior art and is not a part of this invention, handle 11 being illustrated for purposes of evidencing how linear punch 10 would in fact be utilized in its application to achieve an incision in the scalp of a person undergoing hair transplantation.

As indicated in FIG. 2, there is illustrated a partial cross-sectional view of linear punch 10 as illustrated in FIG. 1 as taken along line 2—2. As illustrated in FIG. 2, linear punch 10 is of unitary construction defining a cutting edge 12 that lies in a single plane comprising four separate cutting edges, 12a, 12b, 12c, and 12d (as illustrated in FIG. 5) said four respective cutting edges defining one continuous cutting surface being in the shape of an elongated oval as will be more fully set forth hereinafter. Edge 12 comprising cutting edges 12a, 12b, 12c and 12d respectively is sharpened so as to act as a cutting tool in conjunction with the removal of scalp tissue. Wall member 13 defines an outer structure whose cross section is in the shape of an elongated oval which then tapers into a circular hollow structure as defined by wall member 14, both wall member 13 and wall member 14 defining hollow cavity 15. As depicted in FIG. 2, there is additionally formed opening 16 through wall member 14 so as to allow for the passage of a gas and/or liquid into hollow cavity 15 through opening 16. Wall member 14 is formed so as to be part of base 17, base 17 being structurally affixed to insert member 18, both base member 17 and base member 18 having a circular cross section.

It should be noted that insert member 18, base 17, wall member 14, and wall member 13 all are part of one overall unitary item of construction which make up the linear punch 10. As a result, there is achieved a rugged, structurally integrated tool that is long lasting, reusable, subject to easy sterilization and simple to use. In conjunction with the preferred embodiment of linear punch 10, same is anticipated to be fabricated from stainless steel, although other well known materials utilized in the medical profession that are capable of being sterilized can also be utilized in the fabrication of linear punch 10, nothing herein to be construed otherwise.

As illustrated in FIG. 4, there is depicted a partial cross-sectional view of linear punch 10 as depicted in FIG. 2 taken along line 4—4 wherein there is evidenced a portion of cutting edge 12, to wit, cutting edge 12c of cutting edge 12, cutting edge 12 inclusive of cutting edge 12c as therein illustrated being sharpened in accordance with the invention to provide for the ability of linear punch 10 to cut through scalp tissue.

Additionally, there is further illustrated in FIG. 4 opening 16 which is formed through wall member 14 as well as opening 19 as illustrated in FIG. 3 which is also formed through wall member 14, openings 16 and 19 providing access to the interior of cavity 15 so as to facilitate the cleaning and sterilization of linear punch 10 as well as to facilitate the removal of scalp tissue from hollow cavity 15 in accordance with the invention. It should be noted that although there is illustrated in the preferred embodiment of the invention as illustrated in the drawings the fact that there are two openings, 16 and 19 respectively, formed through wall member 14, nothing herein should be interpreted as to so limit the invention. More particularly, it is within the scope of the invention to have either no such opening formed through wall member 14, one such opening, two such openings or more than two.

In keeping with the invention, linear punch 10 as illustrated in FIG. 1, is inserted into handle member 11 in a manner well known in the prior art, linear punch 10 being secured to handle 11 by the turning of handle 20 which is in threaded mechanical interfit with wall member 21 of handle 11 so as to cause the selective mechanical inter-fit of insert member 18 of linear punch 10 with handle 11 once insert member 18 has been inserted into hollow cavity 22 of handle 11.

Although not part of the invention, handle 11 defines a hollow cavity 22 into which insert member 18 is placed. Once insert member 18 is placed into hollow cavity 22 of handle 11, threaded screw 20 is turned so as to tighten same against insert member 18 as it is positioned within the hollow cavity 22 formed in handle member 11 thereby firmly selectively attaching linear punch 10 to handle 11.

Reference is now herein made to FIG. 5 wherein there is illustrated a bottom view of linear punch 10 constructed in accordance with the invention. More particularly, as illustrated in FIG. 5, cutting edge 12 is therein depicted as defined by wall member 13. As depicted in FIG. 5, cutting edge 12 is comprised of cutting edges 12a, 12b, 12c and 12d. More particularly, cutting edge 12a and cutting edge 12c are parallel to each other. Cutting edge 12b and cutting edge 12d are semi-circular in shape and are opposite each other such that cutting edges 12a, 12b, 12c and 12d form one continuous structure that defines cutting edge 12 as illustrated in the figures. As previously indicated, cutting edge 12 defines an elongated oval, as depicted in FIG. 5, comprised of cutting edge components 12a, 12b, 12c and 12d. In keeping with the invention, and as evidenced in a preferred embodiment thereof, the distance between parallel cutting edges 12a and 12c of cutting edge 12, as compared to the length of cutting edge 12a and cutting edge 12c defines a ratio of 3 to 1. Although nothing herein contained should be considered to limit the scope of the invention to said 3 to 1 ratio, said ratio is, however, envisioned as addressing the preferred embodiment as illustrated in the drawings. Furthermore, FIG. 5 further illustrates the extension of wall member 13 into the structure of wall member 14 as well as illustrative of hollow cavity 15.

In conjunction with the invention, it should be noted that upon the utilization of linear punch 10, the dilation of the surrounding body tissue that is adjacent to the opening created upon the utilization of linear punch 10 in accordance with the invention, will be temporary in nature so as to facilitate the placement of a hair follicle grafted thereto as well as to facilitate the nurturing thereof.

In conjunction with the utilization of linear punch 10 to achieve the transplantation of hair follicles in accordance with the invention, there is placed against the scalp area of a patient where implanting of hair follicles is desired, cutting edge 12 whose sharpened surface will cut through scalp tissue to a depth as determined by the medical personnel utilizing same. Due to the shape of cutting edge 12, linear punch 10 creates an incision in the shape of an elongated oval whose surrounding tissue remains intact. Inherent in the utilization of linear punch 10 is the fact that same does not cause the affected blood vessels of the scalp to cease to bathe the incision in tissue fluid and thus aids in achieving the transplantation of hair follicles-to the transplant area of scalp.

Additionally, the elongated oval shape of cutting edge 12 facilitates the removal of the surface scalp tissue once same is cut so as to allow for the implanting of hair follicles. This is achieved as follows. After there is achieved the initial cut through the scalp tissue of a patient in accordance with the above, linear punch 10 is then angled by causing its vertical axis to no longer be perpendicular to the scalp surface, but rather, is tilted on edge such that cutting edge 12b or cutting edge 12d are utilized to cut beneath the scalp tissue defined by the initial elongated oval cut by having cutting edge 12b or cutting edge 12d traverse the length of said initial elongated oval cut in the scalp tissue at a depth beneath the surface of the scalp as desired. In this manner, there is created an opening in the scalp in the shape of an elongated oval having a desired depth which is capable of receiving the transplantation of hair follicles that will facilitate the growth thereof since the elongated oval opening formed in the scalp will not seek to close upon itself and thus damage the viability of the transplanted hair follicles.

Once an incision in the form of an elongated oval opening has been made in the scalp in accordance with the above by linear punch 10, the incision in the form of an elongated oval opening in the scalp, by its very nature, facilitates the implanting of hair follicles at the proper angle and direction for growth as well as the nourishing thereof by tissue fluids located at the point of implant. By having the incision define an elongated oval shape opening, there is also facilitated the ability to insert therein an aligned series of hair follicles that will not be compressed by the surrounding tissue.

As a result, there is achieved by the utilization of linear punch 10 the ability to transplant hair follicles in a manner and fashion not available by the utilization of prior art devices and techniques in that the utilization of linear punch 10 allows for the bathing in tissue fluid of the transplanted hair follicles to ensure the nourishing thereof, the avoiding of the compressing of the transplanted hair follicles by the surrounding tissue due to the nature of the opening formed in the scalp, the ability to implant hair follicles at the proper angle and direction for growth so as to achieve a natural appearance as related to the transplanted hair follicles and allows for the precise fit into the elongated oval opening formed in the scalp of linear strip grafts of hair follicles created from the harvesting of hair follicles.

It will be understood that the foregoing (general description and the following detailed description as well are exemplary and explanatory of the invention, but are not restrictive thereof.

The accompanying drawings referred to herein and constituting a part hereof, are illustrative of the invention but not restrictive thereof, and, together with the description, serve to explain the principles of the invention.

I claim:

1. A linear punch for utilization in the transplanting of human hair follicles in a patient, said linear punch comprising:
   a support member; and
   a wall member structurally affixed to said support member, said wall member defining at an end opposite said support member a cutting edge having a shape of an elongated oval with continuous rounded ends capable of cutting through exterior scalp tissue of the patient, said wall member additionally defining a hollow cavity.

2. The linear punch of claim 1 wherein said linear punch is fabricated from stainless steel.

3. The linear punch of claim 1, further comprising an insert member and a base member structurally affixed to said insert member, said support member being structurally affixed to said base member.

4. The linear punch of claim 1, wherein the support member defines a hollow cavity, said hollow cavity defined by said support member being contiguous with said hollow cavity defined by said wall member.

5. The linear punch of claim 4, wherein said support member includes a pair of oppositely positioned openings communicating with said hollow cavity defined by said support member.

6. The linear punch of claim 4, wherein said hollow cavity defined by said support member has a circular cross-section.

7. The linear punch of claim 4, further comprising an insert member and a base member structurally affixed to said insert member, said support member being structurally affixed to said base member.

8. A linear punch for utilization in the transplanting of human hair follicles in a patient, said linear punch comprising:
   a support member; and
   a wall member structurally affixed to said support member, said wall member defining at an end opposite said support member an elongated oval cutting edge capable of cutting through exterior scalp tissue of the patient, said elongated oval cutting edge being a continuous cutting edge comprising two parallel cutting edges opposite each other and two semi-circular cutting edges opposite each other and joining the parallel cutting edges, said wall member additionally defining a hollow cavity.

9. The linear punch of claim 8, wherein said two parallel cutting edges both have substantially the same length and are separated by a distance, a ratio of said length of said parallel cutting edges to said distance between said parallel cutting edges being about 3 to 1.

10. A method for forming a site for hair transplantation in a scalp having a surface using a linear punch, the linear punch comprising a support member and a wall member structurally affixed to said support member, said wall member defining at an end opposite said support member a cutting edge having a shape of an elongated oval with continuous rounded ends capable of cutting through exterior scalp tissue of the patient, said wall member additionally defining a hollow cavity, the method comprising the steps of:
   orienting the linear punch generally perpendicular to the scalp surface so that the cutting edge is against the scalp surface and is generally parallel to the scalp surface; and
   applying pressure to the linear punch to force the cutting edge through the scalp surface to thereby create an incision in a shape of an elongated oval with continuous rounded ends in the scalp surface.

11. A method for forming a site for hair transplantation in a scalp having a surface using a linear punch, the linear punch comprising a support member and a wall member structurally affixed to said support member, said wall member defining at an end opposite said support member a cutting edge having a share of an elongated oval with continuous rounded ends capable of cutting through exterior scalp tissue of the patient, said wall member additionally defining a hollow cavity, the method comprising the steps of:
   orienting the linear punch generally perpendicular to the scalp surface so that the cutting edge is against the scalp surface and is generally parallel to the scalp surface;
   applying pressure to the linear punch to force the cutting edge through the scalp surface to thereby create an incision having a length in the scalp surface, the incision having a share of an elongated oval with continuous rounded ends;
   angling the linear punch at a selected angle to the scalp surface which is not perpendicular to the scalp surface at the incision; and applying further pressure to the linear punch so that at least one of the continuous rounded ends of the cutting edge cuts beneath the scalp tissue circumscribed by the incision, the at least one of the continuous rounded ends of the cutting edge traversing the length of the incision.

12. The method of claim 11, wherein the at least one of the two semi-circular cutting edges traverses the length of the incision at a selected depth beneath the scalp surface.

* * * * *